(12) United States Patent
Abbo

(10) Patent No.: US 6,547,729 B1
(45) Date of Patent: Apr. 15, 2003

(54) METHOD AND SYSTEM FOR MEASURING THE AGING OF A SUBJECT

(76) Inventor: Fred E. Abbo, 2402 Paseo Dorado, La Jolla, CA (US) 92037

( * ) Notice: Subject to any disclaimer, the term of this patent is extended or adjusted under 35 U.S.C. 154(b) by 193 days.

(21) Appl. No.: 09/753,914

(22) Filed: Jan. 2, 2001

(51) Int. Cl.[7] ............................................. A61B 5/00
(52) U.S. Cl. ...................................... 600/300; 128/923
(58) Field of Search ................................ 600/300, 301; 128/923, 920, 924, 925

(56) References Cited

U.S. PATENT DOCUMENTS 4,894,547 A * 1/1990 Leffell et al. ............. 250/459.1
6,059,724 A * 5/2000 Campell et al. ............ 128/923

OTHER PUBLICATIONS

Dean, W., "Biological Aging Measurement, Clinical Applications," *The Center for Bio-Gerontology*, Los Angeles, CA Copyright© 1988, 2nd Ed., ISBN 0-93777-00-5.

* cited by examiner

Primary Examiner—Henry C. Yuen
Assistant Examiner—Mahmoud Gimie
(74) Attorney, Agent, or Firm—Baker Botts L.L.P.

(57) ABSTRACT

A method and system are provided for measuring the performance age, rate of aging, and/or useful life span of at least one bodily system of a subject. The method begins with observed values taken from a sample population and expressed as a function of age. A regression curve is determined from this function. The regression curve is solved for a performance age of the at least one bodily system for the subject by using an observed result of the subject's system. A rate of aging of the subject's system is determined from the performance age. A useful life span for the subject's system is determined from the rate of aging. The method may be incorporated into a computer system to automatically determine performance age, rate of aging, and useful life span for one or more bodily systems of one or more subjects.

25 Claims, 2 Drawing Sheets

METHOD AND SYSTEM FOR MEASURING THE AGING OF A SUBJECT

TECHNICAL FIELD OF THE INVENTION

This invention relates generally to the fields of medicine and research and, more particularly to the field of aging measurement.

BACKGROUND OF THE INVENTION

The human body is composed of many component parts or systems. Among other things, these parts include the heart, lungs, brain, kidneys, blood vessels, cells, mitochondria, chromosomes and structural molecules such as DNA, RNA, proteins and collagen.

These systems and/or parts tend to deteriorate with age for various reasons, resulting in impaired function, disease or death. The rate of deterioration is typically different for different parts. Also, the rate of deterioration for a particular part or system may differ between two individuals.

The nature of the various body parts or systems, including their rate of deterioration, provides some insight in connection with determining a strategy for lengthening the usefulness of a particular part or system. Also, advanced knowledge regarding body components or systems aids in diagnosing medical conditions and developing a plan for improving and maintaining the health of an individual or group.

Related to measuring the rate of aging is the concept of developing "biomarkers" of aging. Biomarkers are biochemical indicators of exposure, response and susceptibility. Reliable methods of measuring biomarkers are needed for a variety of reasons, including assessing the effectiveness of potential anti-aging therapies.

One method of measuring the rate of aging is the extension of maximum lifespan. For example, if the maximum lifespan of a strain of mice is about three years of age under natural conditions, and scientists are able to get some of these mice to live for four-to-five years by restricting their food intake, it is convincing evidence that the aging process has been slowed in these mice. One problem with this type of study, however, is that it takes a long time to develop. Obviously, a similar study with humans would take much longer.

Typically, methods directed toward measuring the rate of aging are concerned with "chronological age." "Chronological age" can be defined as an indication of our number of years in existence. However, chronological age is only one way to determine age and it is, at best, only a rough indication of the level at which a subject's bodily systems are performing.

SUMMARY OF THE INVENTION

The present invention provides, among other things, a method and system for assessing the health of a subject. According to the various embodiments, the performance age, rate of aging and useful life span of one or more of a subject's bodily systems may be measured. The "performance age" of a subject's bodily system may be defined as the age at which the bodily system would be considered as functioning and aging normally. The "performance age" of a subject's bodily system may be higher, lower, or equal to the chronological age of the bodily system.

According to one embodiment, a method is provided for assessing the health of a subject. In a first step, a first set of observed values, corresponding to chronological age, is obtained from a sample population for a first bodily system. Next, a first regression curve is determined from the first set of observed values. The first regression curve may be expressed as the chronological age being a function of the first set of observed values. Next, a first performance age of the subject's first bodily system is determined by solving the first regression curve for the first performance age using a first subject observed value for the subject's first bodily system.

According to additional steps of this embodiment, a first rate of aging of the subject's first bodily system may be determined from the slope of the first regression curve. Further, a first useful life span may be determined by comparing the subject's first rate of aging with an average end of useful life of the sample population's first bodily system.

According to various aspects, the foregoing analysis may be extended to a second bodily system to determine a second performance age, second rate of aging, and second useful life span of the subject's second bodily system. The method may be enhanced by prescribing at least medical initiative directed toward improving one or more of the first and second performance ages, first and second rates of aging, and first and second useful life spans. Any bodily system capable of being measured with respect to at least some associated indicator may be assessed, including organs, tissues, cells, and molecules.

According to a second embodiment a system may be provided for assessing the health of a subject. The system may include a processor and a memory coupled to the processor. The system may also include a computer program application located within the memory. The computer program application is executable by the processor. Preferably, the computer program application includes an analysis module, which is adapted to calculate a first performance age of the subject.

The analysis module may also be adapted to calculate a first rate of aging and a first useful life span of the subject's first bodily system. The analysis module may calculate the first performance age by solving a first regression curve using a first subject observed value for the subject's first bodily system. The first regression curve is determined by obtaining, from a sample population, a first set of observed values, corresponding to chronological age, for a first bodily system of the sample population. The first regression curve may be expressed as chronological age being a function of the first set of observed values.

The system may also include a database for storing information concerning a first set of observed values for a first bodily system of a sample population. The database may also store information concerning observed values for one or more subjects' first bodily systems. The computer program application may also include a recommended treatment module for identifying one or more predetermined medical initiatives based on one or more of the first performance age, the first rate of aging, and the first useful life span.

Other aspects of the present invention will be apparent from the drawings, detailed description, and the claims.

BRIEF DESCRIPTION OF THE DRAWINGS

For a more complete understanding of the invention, and for further features and advantages, reference is now made to the following description, taken in conjunction with the accompanying drawings, in which.

DETAILED DESCRIPTION OF EMBODIMENTS OF THE INVENTION

Figure 1:
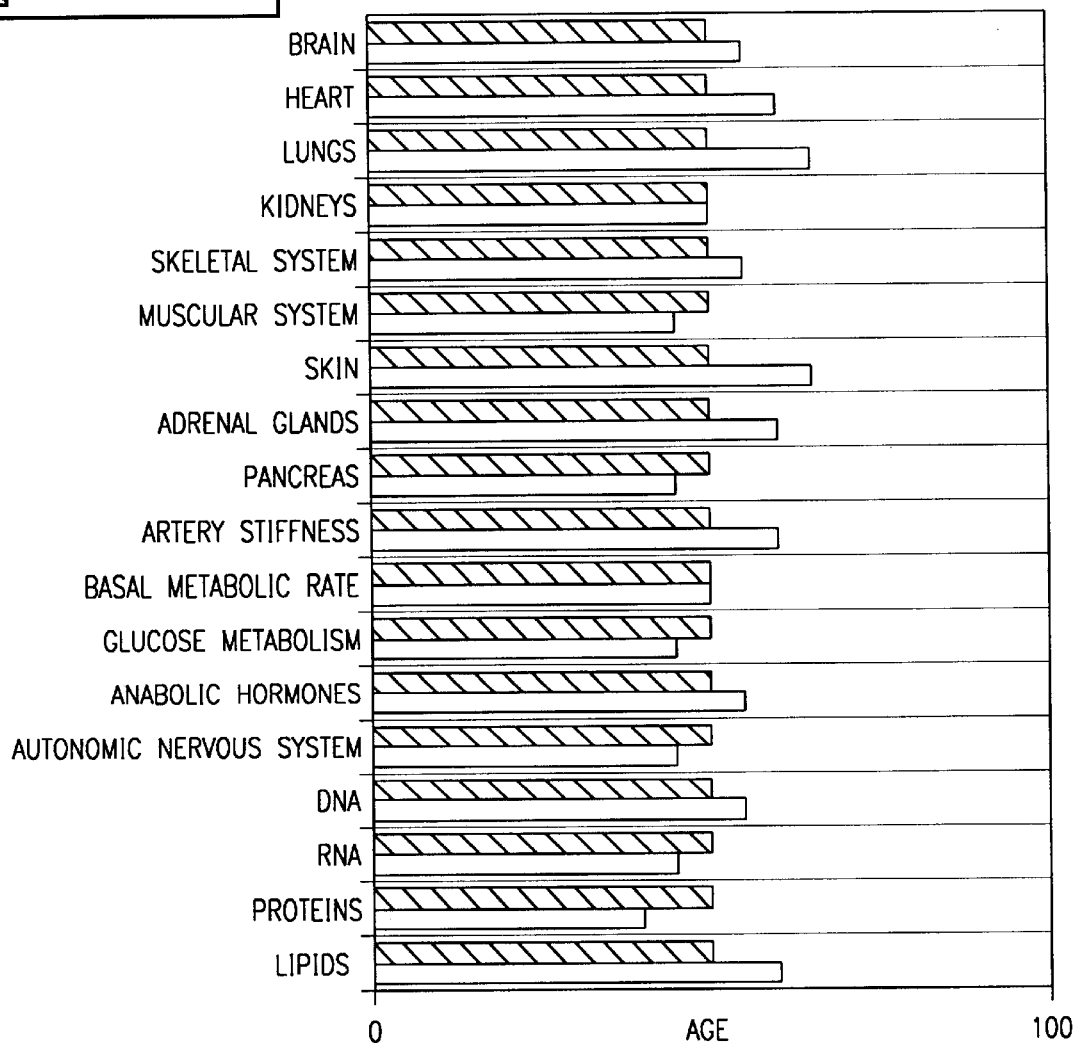
FIG. 1 is a graph depicting an example comparison of performance age versus chronological age for multiple bodily systems of a subject in accordance with an embodiment of the present invention.

Embodiments of the present invention and their advantages are best understood by referring now to FIGS. 1–5 of the drawings, in which like numerals refer to like parts. The present invention provides, among other things, a method and system for measuring the performance age, rate of aging, and useful life span of the various bodily systems within a subject. These bodily systems include, but are not limited to, organs, tissue, cellular systems and molecular systems. A subject, as referred to herein, may be any living organism. As an example, the invention is described in connection with human beings.

In a preferred embodiment, observed values are determined from test results taken from a sample population and are plotted against age. This is done for at least one bodily system. However, a database may be maintained to plot observed values from test results for multiple bodily systems from the same sample population. Preferably, each individual in the sample population studied with relevant lab tests such as, for example, kidney function, heart structure or function, amount of protein damage, lung function, etc. Alternatively, observed test results for different bodily systems may be measured and plotted from different sample populations. A "sample population" may be defined as a group of men or women, in a specified age range (e.g., age 20–95) with a specified ethnic composition, and a specified geographic location. An observed value may be any measurement of a suitable indicator associated with the assessment of the particular bodily system. Some examples of different types of "observed values" include:

(a) For the lungs: Forced Vital Capacity (FVC).

(b) For the heart: Ejection fraction; length of time completed on a treadmill stress test.

(c) For the kidneys: creatinine clearance test.

(d) For proteins: level of Glycosylation of Hemoglobin.

(e) For endocrine glands: load level of biologically active testosterone; level of Dehydroepiandrosterone sulfate; ratio of urinary 17-ketosteroids/17-hydroxycorticosteroids; Growth Hormone: IGF-1.

(f) For the nervous system, including brain: memory tests, reaction time; serial key tapping; digit recall test; letter fluency; category fluency; nerve conduction velocity.

(g) For hardening of the arteries: pulse wave velocity; ankle-brachial index.

(h) For the skeletal system: bone mineral density.

Next, a linear or multiple regression curve is determined where "chronological age" is an independent variable. This can be accomplished using known statistical methods.

Next, using the regression curve obtained in this manner, the variables defining the regression curve may be rearranged so that "performance age" becomes a dependent or "response" variable and an "observed value" becomes an independent or "predictor" variable. With the rearranged equation, one can enter the observed value for a subject, and solve the regression curve for the "performance age" of the particular bodily system being measured for that subject.

The results may be presented to the test subject in an easy-to-understand form, such as a graph, depicting the performance age of the system being measured, compared to the subject's chronological age. An example of this graphical presentation is provided in FIG. 1. In this manner, the subject is provided with a meaningful estimate of the actual performance age of his/her body and it's various bodily systems. Other values, such as rate of aging and end of useful life (as discussed further below) may be similarly represented in a graphical format.

From the above performance age results, the "rate of aging" may be calculated. The rate of aging may be expressed as the rate of change of the observed value for the particular system. Preferably, this is accomplished with respect to every measured system of the subject. The subject can thus be provided with a meaningful estimate of his/her rate of aging.

By extrapolating the rate of aging to an average "end of useful life" for the sample population's corresponding bodily system, one may estimate the useful life span of the bodily system for the particular subject. Finally, one or more medical initiatives may be prescribed based on the foregoing assessment in order to improve the performance age, rate of aging, and/or useful life span of the subject's bodily system. Such medical initiatives may include, but are not limited to, changes in lifestyle, prescriptions of drugs, and or medical procedures. The medical initiatives are thus aimed at extending the life span of the subject.

The invention may be applied to many different bodily systems including, but not limited to, organs, tissues, cells, and molecules. Some examples include, but are not limited to, the following. At the organ level, the invention may be applied to evaluate such organs as the central nervous system or brain, peripheral nervous system (including the parasympathetic nervous system and the sympathetic nervous system), heart, kidneys, stomach, intestines, lungs, endocrine glands (including pituitary and hypothalamus glands, adrenal cortex, adrenal medulla, thyroid, pancreas, ovaries, testicles, and pineal), eyes, and prostate. At the tissue level, the invention may be applied to, for example, muscles, skin, connective tissue (such as collagen, elastin and cartilage), immune system, arteries, and bones. At the cell level, the invention may be applied to, for example, cell walls, mitochondria, and chromosomes. At the molecular level, the invention may be applied to, for example, DNA, RNA, lipids, proteins (including structure proteins and enzymes), oxidants, and anti-oxidants.

According to the first step of the preferred embodiment, a first set of observed values are obtained, from a sample population, for a first bodily system. This may also be accomplished for multiple bodily systems. For a given system, the observed value, (y), may be expressed as a function of chronological age, f(age). This is a statistical regression function, preferably obtained experimentally from a sample population. For instance, the results may be obtained from a large population study. This function may be expressed as:

$$y=f(\text{age}) \text{ or } y=f(x) \tag{1}$$

In this equation, "y" is the "observed value" or test result, "x" is the chronological age of the sample subjects, and f(x) is the regression function.

According to the second step, a linear regression curve is obtained. This may be accomplished by first solving the above equation (1) for "x." Thus, $$x=f(y) \text{ or age } f(y) \tag{2}$$

or a linear regression curve:

$$y=a+bx \tag{3}$$

where "a" and "b" are constants.

According to the third step, the "performance age" of a given system is calculated by solving the equation:

$$x=(y-a)/b \tag{4}$$

In this equation, "x" is the performance age of a particular subject's bodily system, and "y" is the observed value for the particular subject. The coefficients "a" and "b" are determined from the regression function. The coefficient "a" is determined from the regression curve (equation 3) as the y-intercept of that curve. That is, "a" is the value of "y" when "x" equals zero on the plot of the regression curve. The coefficient "b" is equal to the slope of the curve. This value can be obtained by identifying two points on the curve, e.g., (x1, y1) and (x2, y2). The slope is then equal to (y2−y1)/(x2−x1).

Similarly for a multiple regression curve, such as a quadratic regression curve, $$y=a+bx+cx^2 \text{ or} \tag{6}$$

$$x=(-b+\sqrt{b^2-4a(c-y)})/2a \tag{7}$$

The age-level of performance of a subject's tested body system, i.e., the performance age, "x", is thus calculated from the observed value "y", with the known regression coefficients "a," "b," and "c."

To determine the rate of aging (dy/dx), one may take the differential of equation (3) above and conclude that:

$$dy/dx=b \tag{8}$$

where "b" is the slope of the linear regression curve.

To calculate a predicted longevity, or "useful life span," of the particular bodily system, one may compare the rate of aging to an average "end of useful life" for the sample population's corresponding bodily system. For example, one can plot a line using the rate of aging, the chronological age, and the performance age. The chronological age ("x") and performance age ("y") are coordinates of a point on the line, and the particular determined rate of aging is the slope of that line. Therefore:

$$y=y_o+S(x-x_o) \tag{9}$$

where $x_o$ and $y_o$ are the coordinates of a point on the line (for example, the chronological age and corresponding performance age of a particular bodily system of a given subject) and S is the slope of the line. One may then substitute for "y" a reasonable performance level corresponding to the "end of useful life" of the system. One may then solve the equation for "x," which is the projected chronological age at which the particular subject's system will reach the end of it's "useful life span."

As an example of the method discussed above in connection with the preferred embodiment, one may consider a patient, "Joseph" who is 50 years old (chronologically). One may wish to determine the performance age, rate of aging, and projected useful life span of Joseph's kidneys. From a sample population, one might determine that the average observed value for the kidney function, expressed as a function of chronological age, can be represented by the equation y=135−x. For example, an average 30-year-old would expect an average kidney function observed value of y=135−30 or y=105.

Joseph's kidney function, determined by testing, might have an observed value of 60. Thus 60=135−x, or x=135−60, or x=75 (where 75 is the performance age of Joseph's kidneys.

To calculate the rate of aging for Joseph's kidneys, one first determines, from the sample population, that the rate of aging for the sample population is the slope "b" of the regression curve. For the given sample population, it might be determined that the average observed value for the kidney function decreases by one unit each year. Thus, dy/dx=b=−1. Returning to the equation (3) above, y=135+bx, one can substitute Joseph's particular observed value ("y") and his chronological age ("x") and solve the equation for "b" to arrive at the rate of aging of Joseph's kidneys. Thus, 60=135+50b or b=−1.5 Therefore, Joseph's kidneys are aging at a rate of 1.5 units per year as opposed to the average one unit per year.

To determine the projected useful life span of Joseph's kidneys, one uses the equation (9) above. Thus, $y=y_o+S(x-x_o)$. Substituting $y_o$=60, $x_o$=50, and S=−1.5, one arrives at the equation y=60+(−1.5)(x−50), or y=60−1.5x+75, or y=135−1.5x. One might determine, from the sample population or from clinical information, that the average observed value for the kidney function of a kidney that has reached the end of its useful life span, is 20. Then, 20=135−1.5x, or x=(20−135)/(−1.5), or x=76.7, where x is the anticipated chronological age at which Joseph's kidneys can be expected to reach the end of their useful life span.

Figure 2:
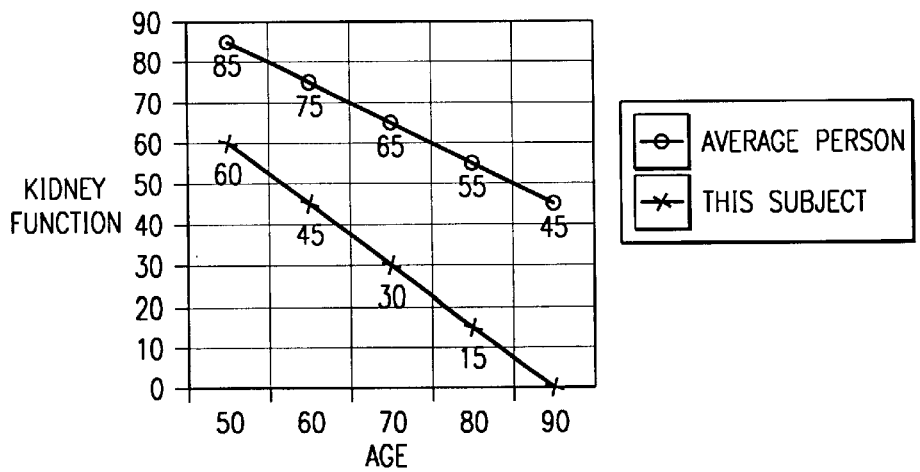
FIG. 2 is graph depicting a comparison of a subject's rate of aging for a bodily system of a subject versus an average rate of aging for the corresponding bodily system of a sample population, in accordance with an embodiment of the present invention.
Figure 3:
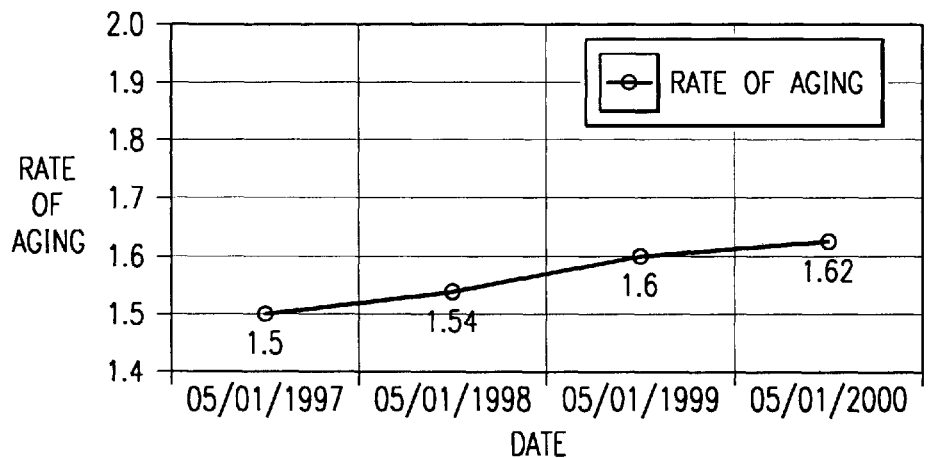
FIG. 3 is a graph depicting changes, over a period of time, in the rate of aging of a bodily system for a subject, in accordance with the present invention.

This example analysis is reflected, in part, by the graph provided in FIG. 2. In FIG. 2 the curve for the sample population is provided above the curve for Joseph's kidneys. It can be seen that, at age 50, the observed value for Joseph's kidney function is 60. If one then looks at the sample population (or "average person") curve, one can see that the average age corresponding to an observed value of 60 is 75. Similarly, by comparing any two points on Joseph's curve, one can see that the rate of aging of Joseph's kidneys is −1.5 units per year, as opposed to the −1 units per year for the average person. Also, knowing that the observed value for an average kidney at the end of its useful life span is 20, one can look at Joseph's curve and see that, at a value of 20, Joseph's chronological age is approximately 76.7 years.

According to certain additional aspects of the present invention, the performance age, rate of aging, and projected useful life span of many different bodily systems are measured and the results are coupled to determine a performance profile for an individual. This profile may thus comprise performance ages for one or more systems at the organ, tissue, cellular, or molecular level. Alternatively, the profile may comprise performance ages for one or more bodily systems from a combination of all or some of these levels. Thus, for example, the profile could include performance ages for multiple organs or performance ages from one or more organs and one or more tissues. Similar combinations of data, for a given individual, may be collected with respect to rate of aging and projected useful life span.

Also, based on the foregoing analysis, one or more medical initiatives may be prescribed directed toward improving performance age, rate of aging, and/or useful life span of a subject's bodily systems. For example, these initiatives may include changes in lifestyle, medicine, and/or medical procedures prescribed to improve performance age, rate of aging, and/or projected useful life span of an individual or one or more of an individual's particular bodily systems. Further, the above analysis and recommended changes can be applied to groups of people. This has particular utility where certain groups of people have similar characteristics or face similar environments.

Further, one may repeat the analysis described above for a given individual (or a group) at several instances over a period of time. This is reflected in the graph provided in FIG. 3. This graph reflects a rate of aging analysis for Joseph, the above example subject, on a yearly basis over a four-year period. The results can be used to determine changes in performance age, rate of aging, projected useful life span. The results can also be used to analyze the effectiveness of various treatments prescribed for the given individual.

According to another embodiment of the present invention, a computer system is used to store data pertaining to the sample population(s), store data pertaining to a given individual (or group), to execute a software program for calculating the performance age, rate of aging, and/or projected useful life span of one or more bodily systems, and to present the resulting analysis in an easy-to-understand report format.

Figure 4:
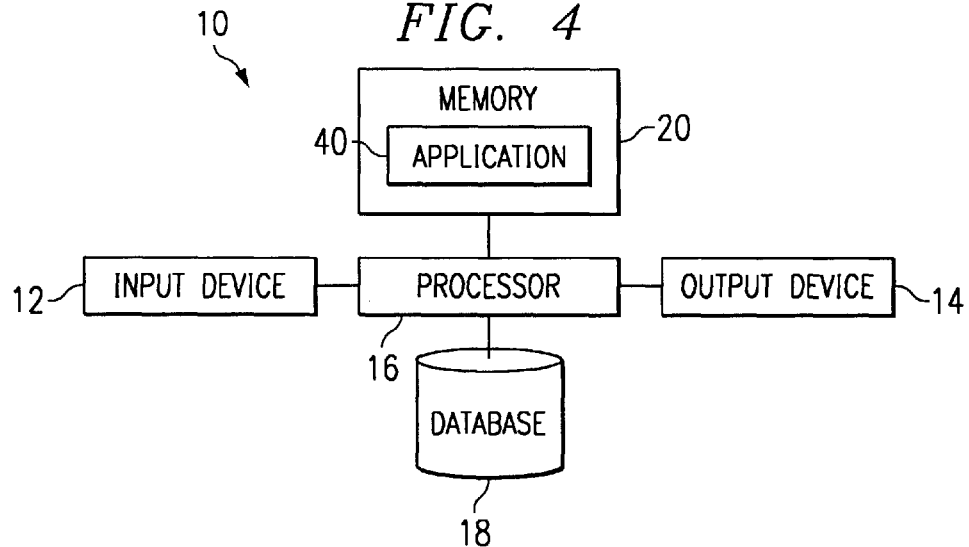
FIG. 4 is a diagram of a system for assessing the health of a subject in accordance with an embodiment of the present invention.

According to this embodiment, and as shown in FIG. 4, a system 10 may be provided. System 10 may comprise an input device 12, an output device 14, a processor 16, a database 18, and memory 20. Input device 12 may include a pointing device such as a mouse, a track pad, a keyboard, and the like. Also, input device 12 may include a combination of these devices. Output device 14 may include a monitor, a printer, and the like, or any combination of these devices.

Memory 20 includes computer software that may be executed by processor 16. The computer software may generally be identified by modules in memory 20. It will be understood that the computer software may be otherwise combined and/or divided for processing within the scope of the present invention. Accordingly, labels of the modules for illustrative purposes and may be varied and still remain within the scope of the present invention. Also, while only one processor is depicted, it should be understood that the system 10 may comprise multiple processors. Further, any appropriate software platform may be utilized including functional or object-oriented programming.

The computer software may be loaded into memory 20 from disk storage (not explicitly shown). Disk storage may include a variety of types of storage media. For example, disk storage may include floppy disk drives, hard disk drives, CD-ROM drives, or magnetic tape drives.

Database 18 includes computer records that may be generally identified by tables. It will be understood that the computer records may be otherwise combined and/or divided within the scope of the present invention. Accordingly, labels of the tables are for illustrative purposes and may be varied while remaining within the scope of the present invention.

Figure 5:
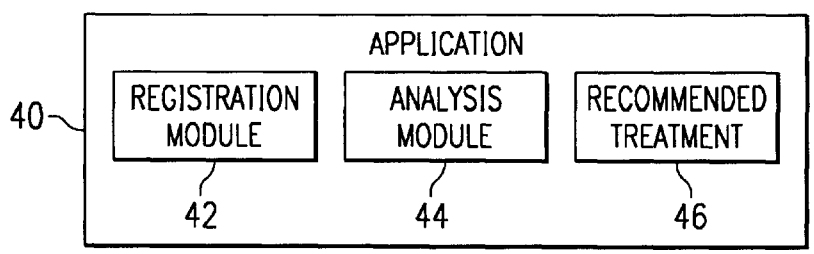
FIG. 5 is a diagram of a component of the system depicted in FIG. 4.

As shown in FIG. 5, system 10 includes a computer program application 40 designed to automatically analyze performance age, rate of aging, and/or projected useful life span of one or more bodily systems of an individual or group. Preferably, application 40 is capable of performing any or all of the various analyses described herein. Application 40 can be run on any number of computing platforms in a variety of computing environments including standalone computers or networks.

Preferably, application 40 provides a registration module 42 which accepts information for a particular individuals or group of individuals and stores this information in a discrete data file. This information may include such items as name, address, telephone numbers, E-mail address, insurance companies and identification numbers, and emergency contact information.

Application 40 also includes an analysis module 44 for evaluating observed values for one or more bodily systems and determining, from the observed values, the performance age, rate of aging, and/or projected useful life span of the one or more bodily systems. To achieve this function, analysis module 44 preferably receives as input, either directly or from a data storage device, fields of data relating to observed values of particular bodily systems for the individual or each individual within the group being evaluated.

Application 40 may also include a recommended treatment module 46. Module 46 may be loaded with one or more predetermined treatment programs corresponding to various calculated values of performance age, rate of aging, and/or projected useful life span. For example, if an individual's performance age for kidneys is 75 when the individual's chronological age is 60, the recommended treatment module may automatically suggest a treatment program designed to reduce the performance age of the kidneys. The recommended treatment module may interface with other modules and or databases within system 10 to determine a recommended treatment. For instance, module 46 might normally respond to a calculated performance age by suggesting a predetermined recommended treatment program including a particular medication. System 10 may be configured such that module 46 first interfaces with an information database that indicates the particular individual is allergic to the particular medicine. Module 46 may be designed such that an alternative treatment is recommended. As another example, the recommended treatment for one bodily system may conflict with the recommended treatment for another bodily system. System 10 may be configured to recognize such conflicts in recommended treatments and adjust treatments or propose alternative recommended treatments accordingly.

Application 40 preferably outputs to a memory device, storage device, and/or a display. For instance, application 40 may output results to a display to provide a presentation of information regarding performance age, rate of aging, and/or projected useful life span. As another example, application 40 may output such information to a storage device, such that this information may be combined with later-calculated values to determine trends and progress as described above.

System 10 is preferably configured to provide, in either hard-copy or electronic format, a presentation of any of the various analyses performed in connection with an individual or group. Such information preferably includes at least a graphical representation of the chronological age compared to the performance age for one or more bodily systems of the individual or group. The presentation may also include one or more recommended treatment programs. These treatment programs may include any number of recommendations including medication, medical procedures, activities, diets, etc. aimed at improving any, or all, of the performance age, rate of aging, and/or projected useful life span of one or more bodily systems.

Although embodiments of the invention and their advantages have been described in detail, a person skilled in the art could make various alterations, additions, and omissions without departing from the spirit and scope of the present invention as defined by the appended claims.

What is claimed is:

1. A method of assessing the health of a subject, comprising the steps of:

obtaining, from a sample population, a first set of observed values, corresponding to chronological age, for a first bodily system of the sample population;

determining a first regression curve from the first set of observed values, wherein the first regression curve is expressed as the chronological age being a function of the first set of observed values; and determining a first performance age of the subject's first bodily system by solving the first regression curve for the first performance age using a first subject observed value for the subject's first bodily system.

2. The method of claim 1, further comprising the step of: determining, from the slope of the first regression curve, a first rate of aging of the subject's first bodily system.

3. The method of claim 2, further comprising the step of: determining a first useful life span of the subject's first bodily system by comparing the subject's first rate of aging to an average end of useful life of the sample population's first bodily system.

4. The method of claim 1, further comprising the steps of:

obtaining, from a sample population, a second set of observed values, corresponding to chronological age, for a second bodily system of the sample population;

determining a second regression curve from the second set of observed values, wherein the regression curve is expressed as the chronological age being a function of the second set of observed values; and determining a second performance age for the subject's second bodily system by solving the second regression curve for the second performance age using a second subject observed value for the subject's second bodily system.

5. The method of claim 4 wherein the first performance age and the second performance age are combined to determine a performance profile of the subject.

6. The method of claim 4, further comprising the steps of:

determining, from the slope of the second regression curve, a second rate of aging of the subject's second bodily system; and determining a second useful life span of the subject's second bodily system by comparing the subject's second rate of aging to an average end of useful life of the sample population's second bodily system.

7. The method of claim 6, further comprising the step of: estimating the subject's life span based on the first useful life span of the subject's first bodily system and the second useful life span of the subject's second bodily system.

8. The method of claim 1, wherein the first bodily system is an organ.

9. The method of claim 1, wherein the first bodily system is a tissue.

10. The method of claim 1, wherein the first bodily system is a cell.

11. The method of claim 1, wherein the first bodily system is a molecule.

12. The method of claim 1, wherein the subject is a human being.

13. A method of treating a subject, comprising the steps of:

determining a first performance age of a first bodily system of the subject;

determining, based on the first performance age, a first rate of aging of the subject's first bodily system;

determining, based on the first rate of aging, a first useful life span of the subject's first bodily system; and prescribing a medical initiative directed toward improving one or more of the subject's first performance age, first rate of aging, or first useful life span.

14. The method of claim 13, further comprising the step of:

monitoring, over a period of time, an effectiveness of the prescribed medical initiative.

15. The method of claim 13, further comprising the step of:

determining a second performance age of a second bodily system of the subject.

16. The method of claim 15, further comprising the steps of:

determining, based on the second performance age, a second rate of aging of the subject's second bodily system; and determining, based on the second rate of aging, a second useful life span of the subject's second bodily system, wherein the medical initiative is directed toward improving one or more of the first and second performance ages, the first and second rates of aging, and the first and second useful life spans.

17. The method of claim 13, wherein the first performance age is determined by solving a first regression curve using a first subject observed value for the subject's first bodily system, and wherein the first regression curve is determined by obtaining, from a sample population, a first set of observed values, corresponding to chronological age, for a first bodily system of the sample population, and expressing chronological age as a function of the first set of observed values.

18. The method of claim 17, wherein the first rate of aging is determined from the slope of the first regression curve.

19. The method of claim 18, wherein the first useful life span is determined by comparing the subject's first rate of aging to an average end of useful life of the sample population's first bodily system.

20. A system for assessing the health of a subject, comprising:

a processor;

a memory coupled to the processor;

a computer program application located within the memory, the computer program application executable by the processor, wherein the computer program application includes an analysis module, the analysis module adapted to calculate a first performance age of the subject by solving a first regression curve using a first subject observed value for the subject's first bodily system.

21. The system of claim 20, wherein the analysis module is further adapted to calculate a first rate of aging and a first useful life span of the subject's first bodily system.

22. The system of claim 20, wherein the first regression curve is determined by obtaining, from a sample population, a first set of observed values, corresponding to chronological age, for a first bodily system of the sample population, the first regression curve being expressed as chronological age being a function of the first set of observed values.

23. The system of claim 20, further comprising a database for storing information concerning a first set of observed values for a first bodily system of a sample population.

24. The system of claim 23, wherein the database also stores information concerning observed values for one or more subjects' first bodily systems.

25. The system of claim 20, wherein the computer program application also includes a recommended treatment module for identifying one or more predetermined medical initiatives based on one or more of the first performance age, the first rate of aging, and the first useful life span.

* * * * *